United States Patent
Watanabe et al.

(10) Patent No.: US 10,163,529 B2
(45) Date of Patent: Dec. 25, 2018

(54) DISPLAY PROCESSING METHOD AND APPARATUS

(71) Applicants: FUJITSU LIMITED, Kawasaki-shi, Kanagawa (JP); The University of Tokyo, Tokyo (JP)

(72) Inventors: Masahiro Watanabe, Kawasaki (JP); Satoshi Fuchikami, Fukuoka (JP); Yoshimasa Kadooka, Kawasaki (JP); Toshiaki Hisada, Tokyo (JP); Seiryo Sugiura, Tokyo (JP); Takumi Washio, Tokyo (JP); Jun-ichi Okada, Tokyo (JP)

(73) Assignees: FUJITSU LIMITED, Kawasaki (JP); THE UNIVERSITY OF TOKYO, Tokyo (JP)

( * ) Notice: Subject to any disclaimer, the term of this patent is extended or adjusted under 35 U.S.C. 154(b) by 847 days.

(21) Appl. No.: 14/061,387

(22) Filed: Oct. 23, 2013

(65) Prior Publication Data

US 2014/0114633 A1 Apr. 24, 2014

(30) Foreign Application Priority Data

Oct. 23, 2012 (JP) ................................. 2012-234051

(51) Int. Cl.
| | |
|---|---|
| G06F 19/00 | (2018.01) |
| G06T 19/20 | (2011.01) |
| G06T 3/00 | (2006.01) |
| G16H 50/50 | (2018.01) |
| A61B 5/00 | (2006.01) |

(52) U.S. Cl.
CPC ........... *G16H 50/50* (2018.01); *G06T 3/0075* (2013.01); *G06T 19/20* (2013.01); *A61B 2576/023* (2013.01)

(58) Field of Classification Search
None
See application file for complete search history.

(56) References Cited

U.S. PATENT DOCUMENTS

| | | | |
|---|---|---|---|
| 5,810,007 A | 9/1998 | Holupka et al. | |
| 6,556,695 B1 * | 4/2003 | Packer | A61B 5/02007 382/128 |
| 2005/0213849 A1 | 9/2005 | Kreang-Arekul et al. | |
| 2007/0014452 A1 | 1/2007 | Suresh et al. | |
| 2009/0161938 A1 | 6/2009 | Shekhar et al. | |
| 2010/0111389 A1 | 5/2010 | Strobel et al. | |
| 2011/0091087 A1 | 4/2011 | Ibarz et al. | |

FOREIGN PATENT DOCUMENTS

| | | |
|---|---|---|
| EP | 2369553 A2 | 9/2011 |
| JP | 7-284014 | 10/1995 |
| JP | 2003-79620 | 3/2003 |
| JP | 2009-28362 | 2/2009 |

OTHER PUBLICATIONS

Huang et al. (IEEE Transactions on Medical Imaging (2009) vol. 28, No. 8, pp. 1179-1189).*
Mitchell et al. (IEEE Transactions on Medical Imaging (2002) vol. 21, No. 9, pp. 1167-1178).*
Saber et al. (Annals of Biomedical Engineering (2003) vol. 21, pp. 42-52).*
Schaerer et al. (Medical Image Analysis (2010) vol. 14, pp. 738-749.*
Schneider et al. (Medical Image Analysis (2011) Mar. 14, 2011, preprint, pp. 1-10).*
S. Sanjay-Gopal et al., "A regional Registration Technique for Automated Interval Change Analysis of Breast Lesions on Mammograms", Medical Physics, vol. 26, No. 12, Dec. 1999, pp. 2669-2679.
Extended European Search Report dated Mar. 14, 2014 in corresponding European Application No. 13189724.1.
Japanese Office Action dated May 31, 2016 in corresponding Japanese Patent Application No. 2012-234051.
Eto et al., "Automated Mitral Annular Tracking: A Novel Method for Evaluating Mitral Annular Motion Using Two-Dimensional Echocardiography," Journal of American Society of Echocardiography, vol. 18, Issue 4, pp. 306-312, Apr. 2005.
Japanese Office Action dated Jan. 10, 2017 in corresponding Japanese Patent Application No. 2012-234051.

* cited by examiner

*Primary Examiner* — Lori A. Clow
(74) *Attorney, Agent, or Firm* — Staas & Halsey LLP

(57) ABSTRACT

A disclosed method includes: defining two first points in a model cross section of a model of an object and two corresponding second points in an image that is a cross section of the object for a reference time; performing first transforming including expansion or reduction for the model cross section so that a position of a second point is identical to a position of a corresponding first point; superimposing the image and the model cross section after the performing; second transforming a second model cross section for a second time after the reference time, so that positions of two second points in a second image for the second time are almost identical to positions of corresponding two first points in the second model cross section; and superimposing the second image and the second model cross section after the second transforming.

4 Claims, 8 Drawing Sheets

DISPLAY PROCESSING METHOD AND APPARATUS

CROSS-REFERENCE TO RELATED APPLICATIONS

This application is based upon and claims the benefit of priority of the prior Japanese Patent Application No. 2012-234051, filed on Oct. 23, 2012, the entire contents of which are incorporated herein by reference.

FIELD

This invention relates to a display processing technique.

BACKGROUND

Recently, various analyses for human organs, especially, heart are performed. Specifically, blood is output by the cardiac muscle as it contracts stimulated by electric signals. A computational numerical analysis to analyze such phenomena is carried out. Then, according to results of the numerical analysis, the behaviors of the cardiac muscle are displayed by using 3-dimensional computer graphics technique.

On the other hand, in the medical field, different measurement apparatuses for the medical analysis such as an ultrasonic diagnostic equipment, Magnetic Resonance Imaging (MRI) apparatus, Computed Tomography (CT) scan apparatus and the like are used to directly measure information about organs such as by using cross sections of the cardiac muscle of the heart. The information of the cross sections of the heart is 2-dimensional image data, typically.

Because both of them represent the behaviors of the cardiac muscle, however, data formats of both of them are different from each other, both of them can be displayed on right and left in order to compare the results of them. However, it is not easy to display both of them as time goes by while arranging both of them in appropriate positions to superimpose them. Especially, in the ultrasonic diagnosis using the ultrasonic diagnosis equipment, the measurement is performed by placing a probe onto the breast or the abdomen of the patient, by a doctor, where the probe that emits the ultrasonic into the breast or the abdomen of the patient. Therefore, there are problems that strain arises in the measured image and that the cross section is not fixed and the images of the cross section fluctuate.

SUMMARY

A display processing method relating to this invention includes: (A) accepting designation of two first control points in a model cross section that is a cross section of a generated model of an object, wherein each of the two first control points corresponds to either of two second control points in an input image that is obtained by photographing a cross section of the object for a reference time; (B) first performing a first transformation processing that includes expansion or reduction for the model cross section for the reference time so that a position of a second control point for the reference time is identical to a position of a corresponding first control point; (C) first superimposing the input image for the reference time and the model cross section after the first transformation processing to display a first superimposition result; (D) second performing a second transformation processing for a second model cross section for a second time that is a time after the reference time, so that a position of one of two second control points in an input image for the second time is identical to a position of a corresponding first control point in the second model cross section, and another first control point in the second model cross section is on a straight line that passes through the two second control points in the input image for the second time; and (E) second superimposing the input image for the second time and the second model cross section after the second transformation processing to display a second superimposition result.

The object and advantages of the embodiment will be realized and attained by means of the elements and combinations particularly pointed out in the claims.

It is to be understood that both the foregoing general description and the following detailed description are exemplary and explanatory and are not restrictive of the embodiment, as claimed.

DETAILED DESCRIPTION

Figure 1:
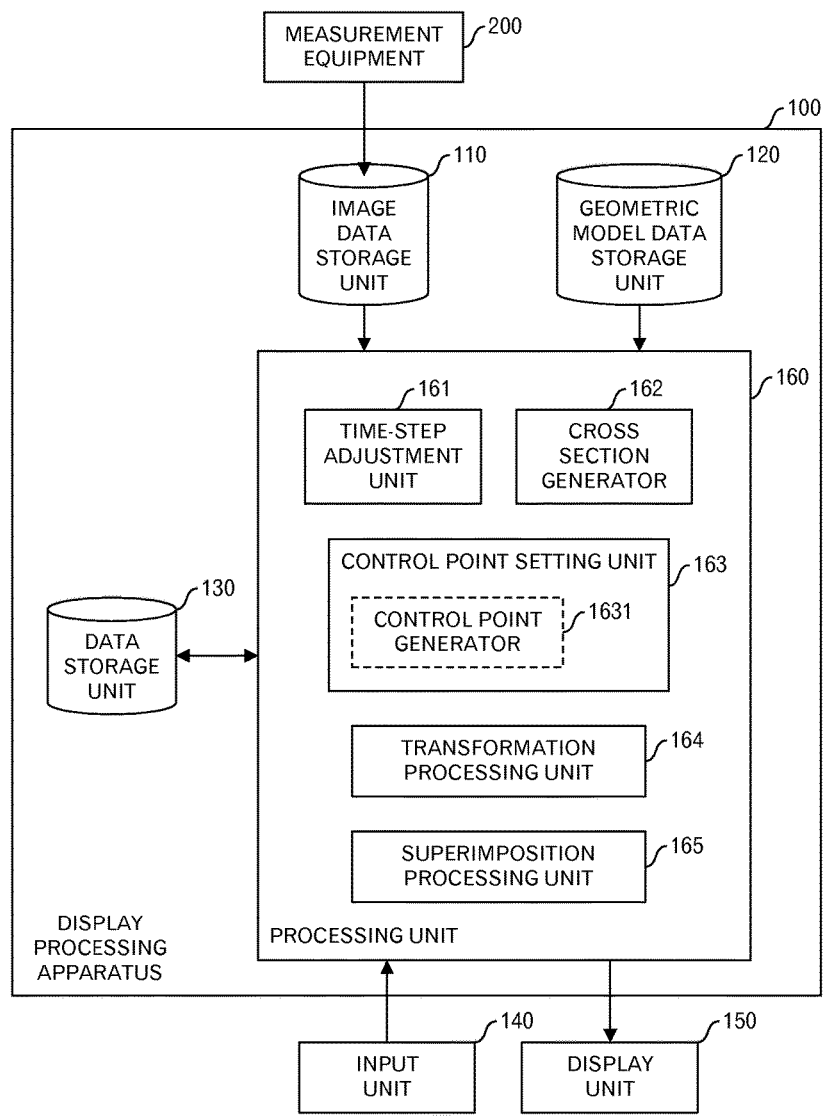
FIG. 1 is a functional block diagram of a display processing apparatus relating to an embodiment.

FIG. 1 illustrates a functional block diagram of a display processing apparatus relating to an embodiment of this invention. The display processing apparatus 100 is connected to measurement equipment 200, such as ultrasonic diagnosis equipment, MRI apparatus, CT scan apparatus or the like, and is also connected to an input unit 140 and display unit 150. Moreover, the display processing apparatus 100 includes an image data storage unit 110 that stores image data received from the measurement equipment 200, a geometric model data storage unit 120 stores data of the 3-dimensional geometric model, a data storage unit 130 that stores data during a processing, and a processing unit 160 that execute the processing relating to this embodiment.

Figure 2:
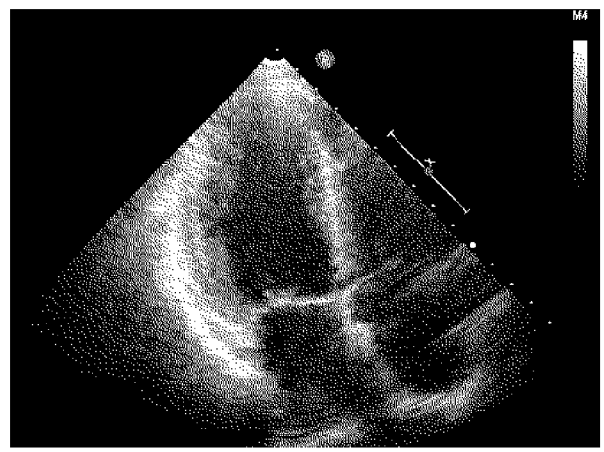
FIG. 2 is a diagram depicting an example of an image of a cross section of the heart.

The image data storage unit 110 stores image data for plural frames that are outputted, for example, by the measurement equipment 200 and arranged at predetermined time intervals. As an example, FIG. 2 illustrates image data for one frame, which is generated by the ultrasonic echo emitted by the ultrasonic diagnosis equipment. The image data illustrated in FIG. 2 represents a cross section of the heart, however, because a doctor fixes the probe, the position of the cross section is not always fixed in the space due to the effect of the breathing and/or the doctor himself. Moreover, because of the lens effect of the ultrasonic signal, the position of the cardiac muscle in the image is not always positioned at a true position of the cardiac muscle. In this embodiment, as one example, a case will be explained in which the image data outputted by the ultrasonic diagnosis equipment is superimposed with the generated geometric model data, however, of course, it is also possible to apply this embodiment to a case in which image data outputted by the MRI apparatus or CT scan apparatus is superimposed with the generated geometric model.

The geometric model data storage unit 120 stores geometric model data (e.g. tetrahedral element data) as a time-series, which is generated for a time period of one beat of the heart, in case of the heart. The geometric model data includes coordinate values for each vertex of the tetrahedral elements used to identify shape, element information, a physical value of each element, and the like.

The processing unit 160 includes a time-step adjustment unit 161, cross section generator 162, control point setting unit 163, transformation processing unit 164 and superimposition processing unit 165. Moreover, the control point setting unit 163 may include a control point generator 1631.

The time-step adjustment unit 161 extracts data of the geometric models so as to synchronize with the image frame, for example, because the number of frames for the image in the period for one beat of the heart is different from the number of time-steps for the generated geometric models.

In response to an instruction from the user, the cross section generator 162 generates cross section data, which corresponds to the cross section of the heart, and which is represented in the image stored in the image data storage unit 110, from data of the geometric model.

For example, in response to an instruction from the user, the control point setting unit 163 sets two points on the image for each frame and corresponding two points on the cross sections of the geometric models, as control points. The control point generator 1631 automatically extracts points corresponding to the annulus from the image in case of the heart. Therefore, when the control points are preset to the annulus, the control point generator 1631 sets the control points. When the control points are set to other points, the user designates the control points.

The transformation processing unit 164 performs at least either of rotation, translation, expansion and reduction for data of the cross sections of the geometric models, for example, as necessary. For example, when the image data outputted by the ultrasonic diagnosis equipment or the like is superimposed on the generated geometric model data, the transformation processing unit 164 performs the transformation processing so that the geometric model data can be superimposed on the image data. The transformation processing unit 164 also performs at least either of the rotation and translation for data for time after the reference time, in addition to the transformation processing for data for the reference time (e.g. initial time).

The superimposition processing unit 165 superimposes cross section data of the geometric model after the transformation processing by the transformation processing unit 164 on the image data for each frame, and causes the display unit 150 to displays the superimposed data.

Next, processing contents of the display processing apparatus 100 will be explained by using FIG. 3 to FIG. 9C.

Figure 3:
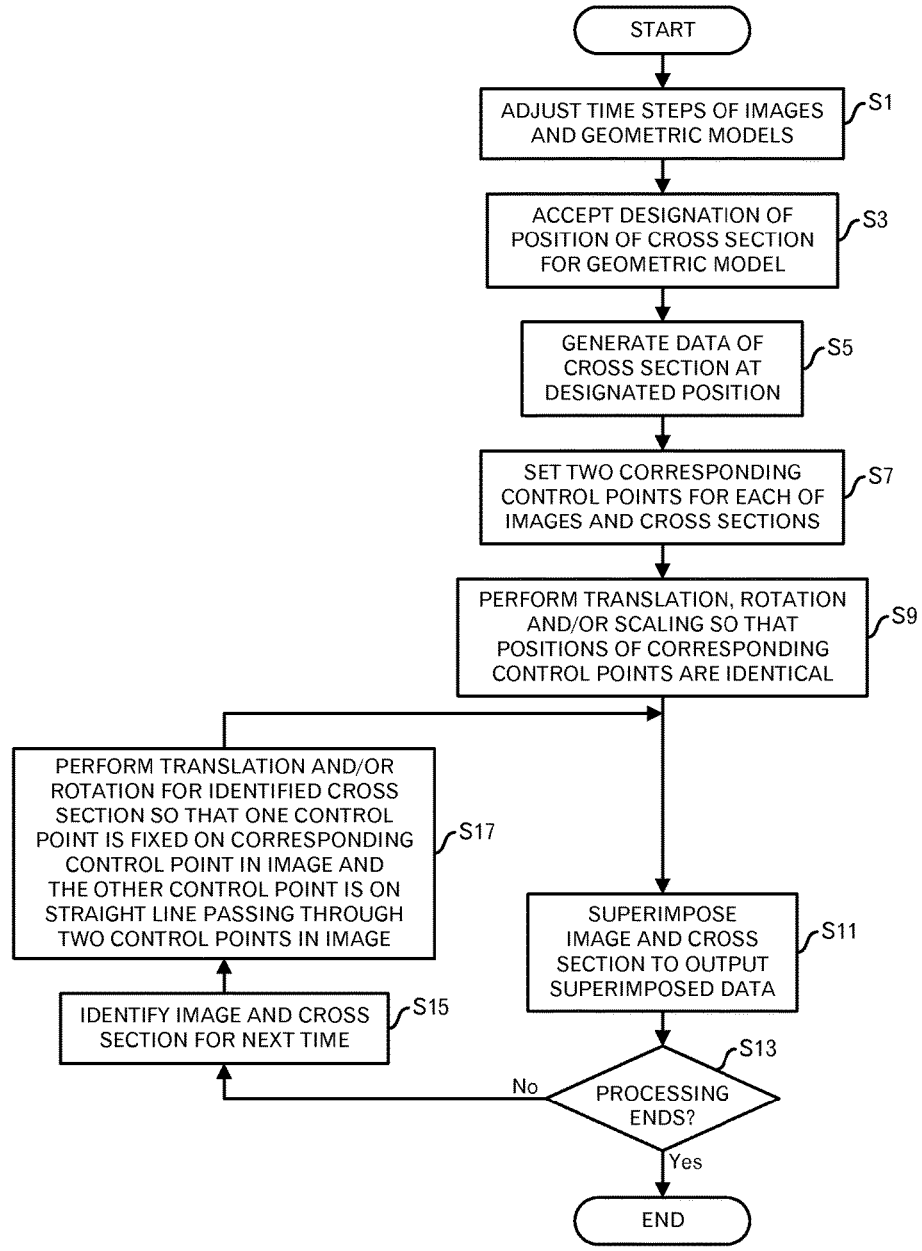
FIG. 3 is a diagram depicting a processing flow of a processing relating to the embodiment.
Figure 4:
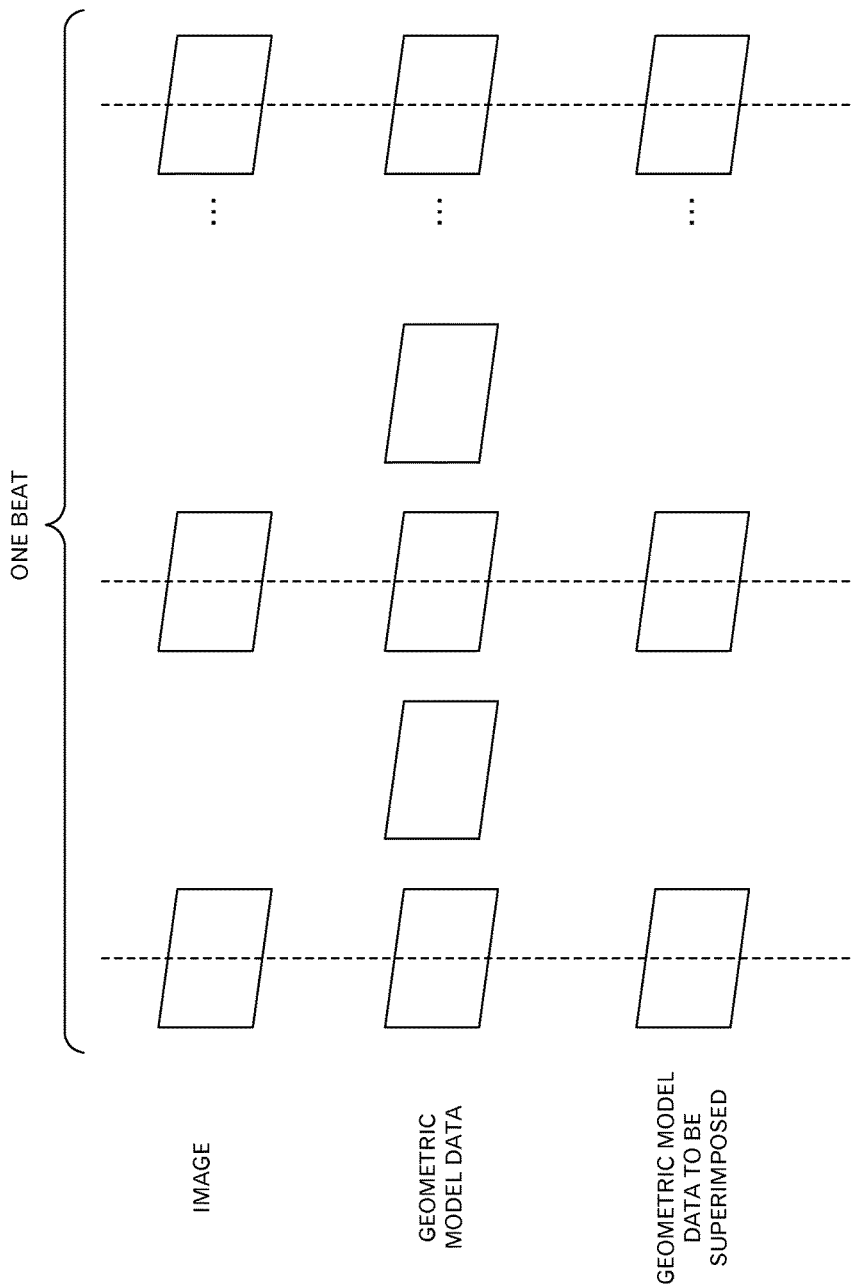
FIG. 4 is a diagram schematically depicting a time-step adjustment processing.

First, the time-step adjustment unit 161 of the processing unit 160 performs a processing to adjust the time-steps of the images and geometric models or model time wise samples from a frame interval of the images stored in the image data storage unit 110 and a time interval of the geometric models stored in the geometric model data storage unit 120 (FIG. 3: step S1). Typically, because the frame interval of the images is longer that the time interval of the geometric models, data of the geometric models is extracted so that the interval of the extracted geometric models becomes identical with the frame interval of the images, for example. This processing will be depicted schematically in FIG. 4. For example, when the image data and the geometric model data are arranged for one beat of the heart, the number of geometric models is greater than the number of frames of the images. Then, by extracting data of the geometric model at the same time (depicted by vertical dotted line in FIG. 4) as each frame of the image, the extracted geometric model is used as the geometric model to be superimposed. In an example of FIG. 4, data of the geometric model at the same time exists, however, if data of the geometric model at the same time do not exist, data of the geometric model at the same time is generated by interpolating the geometric models before and after that time, for example. However, when the difference between timings is little, the geometric model at that timing may be extracted without the interpolation. Moreover, when the interval of the image frames is shorter, the image frames may be extracted so that the interval of the extracted images becomes identical the timing of the geometric model.

Next, the cross section generator 162 of the processing unit 160 prompts the user to designate a cross section corresponding to the cross section of an object, which is represented by the image data, and when the user's designation for the cross section of the geometric model is accepted (step S3), the cross section generator 162 generates data of the cross sections of the geometric models according to the instruction, and stores the data of the cross sections into the data storage unit 130, for example (step S5).

The image of the ultrasonic echo includes movement of organs on the sample plane, however, when considering that no fluctuation in the photographing or capturing is included in a perpendicular direction to the image plane, it is considered or assumed that the image of the ultrasonic echo is data in a fixed space. Therefore, for example, a corresponding cross section in the geometric model at the reference time (e.g. start or initial time) is identified, and the corresponding cross section in the geometric models is fixed to perform a following processing.

When the heart is photographed or imaged by the ultrasonic echo, typically, the cross-section view of the parasternal long-axis and left-side and the cross-section view of the parasternal short-axis and left-side (e.g. aortic level, apex level, papillary muscle level, mitral valve level or the like), the cross-section view of the apical four-chamber, the cross-section view of the apical two-chamber, the transesophageal view or the like are photographed mostly, so the pertinent cross section is designated for the geometric model.

The processing itself to generate data of the cross section of the geometric model is processing that has been executed conventionally (e.g. a function in AVS/Express supplied by AVS Co. Ltd., Paraview supplied by Kitware Inc. or the like), so the detailed explanation is omitted here.

Figure 5:
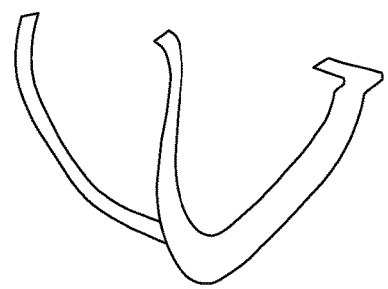
FIG. 5 is a diagram depicting an example of a cross section of a geometric model.

For example, data of the cross section of the geometric model is generated as illustrated in FIG. 5. Here, for each of the geometric models to be superimposed, which were extracted at the step S1, the cross section data is generated. The cross section data is expressed by triangular elements, for example.

Next, the control point setting unit 163 performs processing to set two corresponding control points for each of the cross sections of the geometric models and the images (step S7). As described above, in case of the heart, it is possible to automatically extract the annulus, so when the user designates the annulus as the control point from the input unit 140, the control point generator 1631 identifies control points corresponding to the annulus from the image of each frame. For example, see Yoko Eto, et. al., "Automated Mitral Annular Tracking: A Novel Method for Evaluating Mitral Annular Motion Using Two-dimensional Echocardiography", Journal of the American Society of Echocardiography, pp. 306-312, Volume 18 Number 4, (2005).

Figure 6:
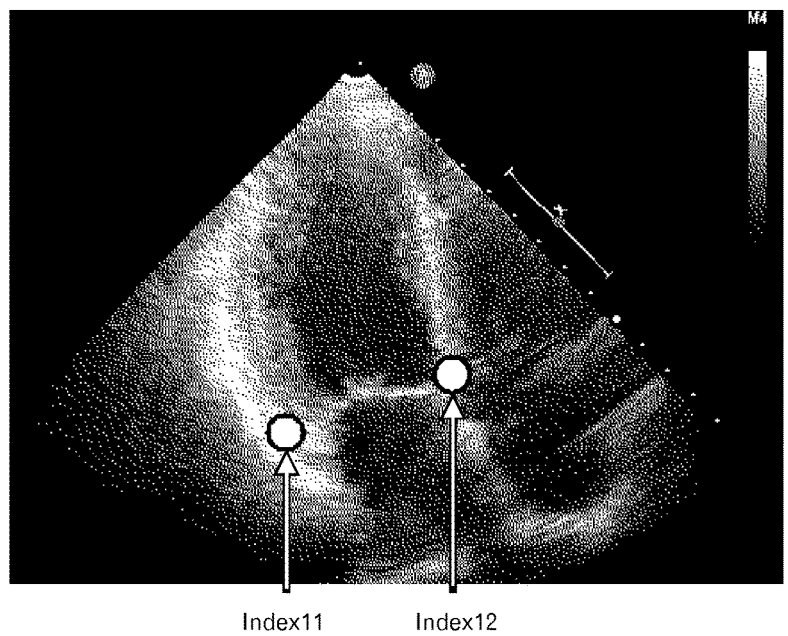
FIG. 6 is a diagram depicting a setting example of control points for the image.
Figure 7:
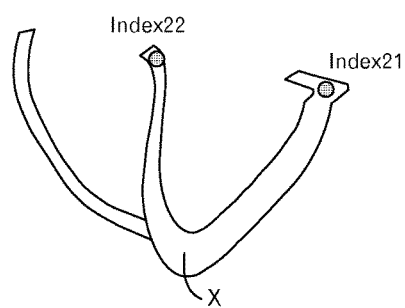
FIG. 7 is a diagram depicting a setting example of control points for the cross section of the geometric model.

In case of the image illustrated in FIG. 2, control points Index11 and Index12 are identified as illustrated in FIG. 6. However, when using the annulus as the control points or using other points as the control points, the user may designate points individually. Furthermore, as schematically illustrated in FIG. 7, on the cross section of the geometric model, a control point Index21 corresponding to the control point Index11 is set according to the user's designation, and a control point Index22 corresponding to the control Index12 is set according to the user's designation. When the control points are set at vertexes of the triangular elements on the cross section of the geometric model at the reference time, the same vertexes of the same triangular elements will be processed as those being selected at each time that is later than the reference time. However, for each of the cross sections of the geometric models to be superimposed, the control points may be set according to the user's designation.

After that, the transformation processing unit 164 performs first transformation processing that includes at least one of the translation, rotation and scaling (e.g. expansion and/or reduction) so that the positions of the corresponding control points become identical, for the cross section of the geometric model to be superimposed for each time, and stores the processing results into the data storage unit 130 (step S9).

More specifically, the coordinates of the control point Index11 in the image at the reference time is ($x_{I\_Index11}$, $y_{I\_Index11}$), the coordinates of the control point Index12 is ($x_{I\_Index12}$, $Y_{I\_Index12}$), the coordinates of the control point Index21 in the cross section of the geometric model at the reference time is ($x_{P\_Index21}$, $y_{P\_Index21}$), and the coordinates of the control point Index22 in the cross section of the geometric model at the reference time is ($x_{P\_Index22}$, $y_{P\_Index22}$). In this case, the scale parameters Sx and Sy are calculated as follows:

$$\Delta x_I = x_{I\_Index11} - x_{I\_Index12}$$
$$\Delta y_I = y_{I\_Index11} - y_{I\_Index12}$$
$$\Delta x_P = x_{P\_Index21} - x_{P\_Index22}$$
$$\Delta y_P = x_{P\_Index21} - y_{P\_Index22}$$
$$Sx = \frac{\Delta x_I}{\Delta x_P}$$
$$Sy = \frac{\Delta y_I}{\Delta y_P}$$

After expanding or reducing the size by using such scale parameters, the translation and rotation are performed so that the position of the control point Index21 becomes identical to the position of the control point Index11, and the position of the control point Index22 becomes the position of the control point Index12. Because the calculation for this transformation processing is well-known, the detailed explanation is omitted.

Because the first transformation processing is basic processing for the superimposition, the first transformation processing is also performed for the cross section of the geometric model to be superimposed for each time other than the reference time. However, only the scaling may be performed for the cross section of the geometric model to be superimposed for each time other than the reference time, and the translation and the rotation may not be performed at this stage. Furthermore, the scaling may also be performed immediately before the processing for making the positions of the control points identical and the like.

Then, the superimposition processing unit 165 generates display data by superimposing the image and the cross section after the first transformation processing for the same time to output the generated the display data to the display unit 150 (step S11).

Figure 8:
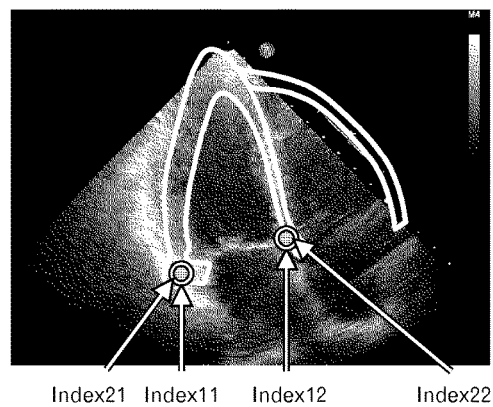
FIG. 8 is a diagram depicting an example of initial superimposition display.

For example, at the reference time, the superimposing display as illustrated in FIG. 8 is performed. As illustrated in FIG. 7, in order to make it easy to view the image data, only contours of the cross section of the geometric model to be superimposed are displayed. The user may select how to display the inside of the contours, and for example, it may be painted over in a predetermined color.

Then, the processing unit 160 determines whether or not an event indicating the processing end is detected, such as the processing end is instructed by the user (step S13). When the event for the processing end is detected, the processing ends.

On the other hand, when the processing does not end, the transformation processing unit 164 identifies image data at a next time or instant in the image data storage unit 110 and cross section data in the geometric model to be superimposed at the next time in the data storage unit 130 (step S15). Then, the transformation processing unit 164 performs a second transformation processing to execute at least one of the translation and rotation for the identified cross section of the geometric model to be superimposed so that one control point (e.g. control point Index22) is fixed on a corresponding control point (e.g. control point Index12) in the image and the other control point (e.g. control point Index21) is on a straight line passing through two control points in the image (step S17).

Because the size of the annulus changes according to the movement of the heart, when the annulus is used as the control point, the scaling is also executed each time a sample is taken in order to make positions of the corresponding control points of the image and cross section of the geometric model to be superimposed for each time after the reference time identical. In this embodiment, in order to simplify the processing, the scaling is carried out for the cross sections for each time after the reference time in the first transformation processing by using the scale parameters at the reference time, and in the second transformation processing, at least either of the translation and rotation is performed for the cross sections for each time after the reference time. However, the first transformation processing by the scale parameters may be included in the second transformation processing.

Figure 9A:
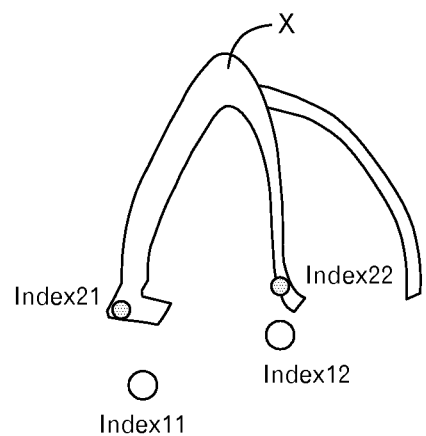
FIG. 9A is a diagram depicting an example of a result of a first transformation processing.
Figure 9B:
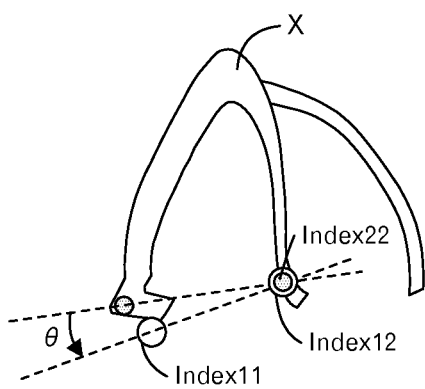
FIG. 9B is a diagram depicting an example of a state in an initial stage of a second transformation processing.
Figure 9C:
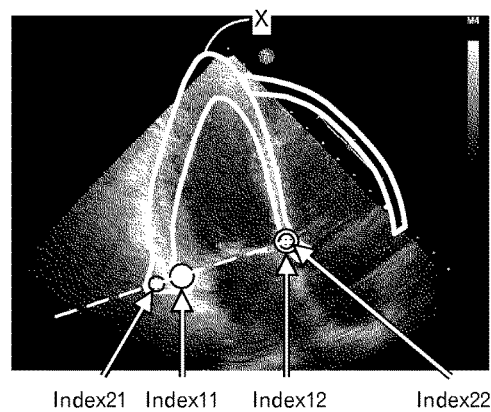
FIG. 9C is a diagram depicting an example of a state in a final state of the second transformation processing.

For example, in the first transformation processing, when the cross section X of the geometric model to be superimposed is arranged as illustrated in FIG. 9A, the translation is performed so as to make positions of the control point Index12 in the image and corresponding control point Index22 in the cross section X of the geometric model to be superimposed for the same time identical. Moreover, the control point Index21 in the cross section X of the geometric model to be superimposed is rotated by an angle θ using the control point Index22 as the center of the rotation so that the control point Index21 is on a straight line passing through the control points Index11 and Index12. Then, as illustrated in FIG. 9C, the control point Index11 is not placed on the control point Index21, however, they are arranged almost at the same position. Moreover, the straight line passing through the two control points Index11 and Index12 has the same direction of the straight line passing through the two control points Index21 and Index22.

After that, the processing shifts to the step S11. In other words, the superimposition processing unit 165 superimposes the cross section data after the second transformation processing and image data to generate data to display the superimposition result.

By repeating such processing, the image obtained from the measurement equipment 200 and data of the same cross section of the geometric model can be superimposed and displayed so as to make it easy to understand the state.

Although the embodiment of this invention was explained above, this invention is not limited to the embodiment. For example, the functional block diagram is a mere example, and a different program module configuration may be employed. Moreover, as for the processing flow, as long as the processing result does not change, the turns of the steps may be exchanged or plural steps may be executed in parallel.

For example, an example was explained in which the first transformation processing and the second transformation processing are performed for the cross section of the geometric model to be superimposed, the transformation processing may be performed for the image. At that time, the reference is the cross section of the geometric model to be superimposed.

Moreover, the first transformation processing may not be performed at the step S9 for the cross sections after the reference time, and the first transformation processing and the second transformation processing may be performed at the step S17. Furthermore, in such a case, when the control points such as the annulus are automatically extracted from the image, this processing may be executed after the step S15 for the images of the frames after the reference time.

Figure 10:
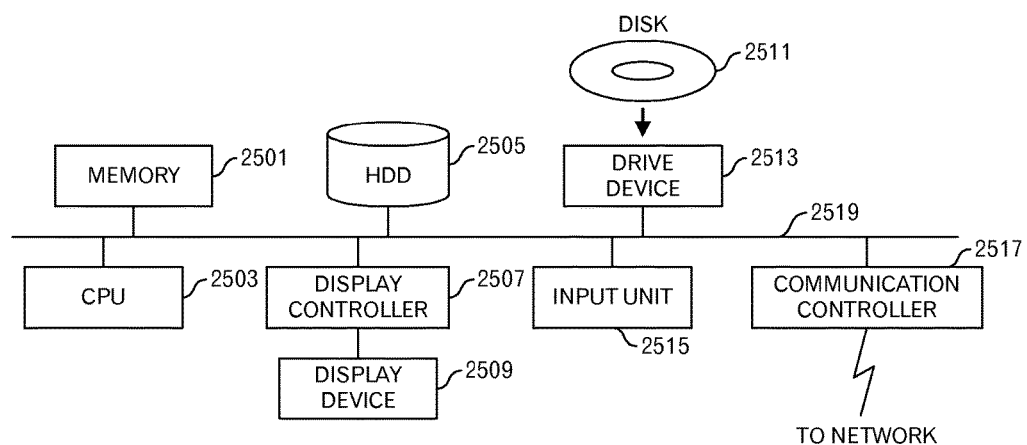
FIG. 10 is a functional block diagram of a computer.

In addition, the aforementioned display processing apparatus 100 is a computer device as illustrated in FIG. 10. That is, a memory 2501 (storage device), a CPU 2503 (processor), a hard disk drive (HDD) 2505, a display controller 2507 connected to a display device 2509, a drive device 2513 for a removable disk 2511, an input device 2515, and a communication controller 2517 for connection with a network are connected through a bus 2519 as illustrated in FIG. 10. An operating system (OS) and an application program for carrying out the foregoing processing in the embodiment, are stored in the HDD 2505, and when executed by the CPU 2503, they are read out from the HDD 2505 to the memory 2501. As the need arises, the CPU 2503 controls the display controller 2507, the communication controller 2517, and the drive device 2513, and causes them to perform predetermined operations. Moreover, intermediate processing data is stored in the memory 2501, and if necessary, it is stored in the HDD 2505. In this embodiment of this technique, the application program to realize the aforementioned functions is stored in the computer-readable, non-transitory removable disk 2511 and distributed, and then it is installed into the HDD 2505 from the drive device 2513. It may be installed into the HDD 2505 via the network such as the Internet and the communication controller 2517. In the computer as stated above, the hardware such as the CPU 2503 and the memory 2501, the OS and the application programs systematically cooperate with each other, so that various functions as described above in details are realized.

The embodiments of this invention are outlined as follows:

A display processing method relating to a first aspect of the embodiments includes: (A) accepting designation of two second control points in a second cross section in a model of an object for a reference time, wherein each of the two second control points corresponds to either of two first control points in an image of a corresponding first cross section of the object for the reference time; (B) performing a first transformation processing that includes expansion or reduction for the second cross section of the model of the object for the reference time so that the positions of the first control point and corresponding second control point are identical or overlap each other; (C) superimposing the image of the corresponding first cross section for the reference time and the second cross section of the model of the object after the first transformation processing to display the superimposition result; (D) performing a second transformation processing for a second cross section of a model of the object for a second time that is a time after the reference time so that a position of one of first control points in an image of a cross section of the object for the second time is identical to a position of a corresponding second control point in a second cross section after the expansion or reduction for the second time, and another second control point in the second cross section after the expansion or reduction for the second time, which corresponds to the other first control point, is on a straight line passing through the two control points in the image of the cross section of the object for the second time; and (E) superimposing the image of the cross section of the object for the second time and the second cross section of the object after the second transformation processing.

According to this method, even after the second time, it is possible to superimpose the cross section of the model of the object and the image of the cross section of the object, appropriately with the simplified processing (i.e. the second transformation processing).

Moreover, the display processing method relating to the first aspect of the embodiment may further include: extracting images of the cross sections of the object or data of the models of the object for the same time according to a time interval of the image of the cross section of the object or a time interval of data of the models of the object. For example, data whose time interval is shorter may be extracted in conformity with data whose time interval is longer.

Furthermore, in the aforementioned first transformation processing, data of the second cross section in the model of the object may be generated for each time, and the first transformation processing may be performed for the second cross section of the model of the object for each time. Thus, it is possible to execute the second transformation processing at high speed. As for the second cross section of the model of the object for each time after the reference time, only the expansion or reduction may be executed. The aforementioned expansion or reduction may be performed as part of the second transformation processing instead of the first transformation processing.

A display processing method relating to a second aspect of the embodiments includes: (A) accepting designation of two second control points in a second cross section in a model of an object for a reference time, wherein each of the two second control points corresponds to either of two first control points in an image of a corresponding first cross section of the object for the reference time; (B) performing a first transformation processing that includes expansion or reduction for the image of the corresponding first cross section of the object so that the positions of the first control point and corresponding second control point are identical or overlap each other; (C) superimposing the image of the corresponding first cross section for the reference time after the first transformation processing and the second cross section of the model of the object to display the superimposition result; (D) performing a second transformation processing for an image of a cross section of the object for a second time that is a time after the reference time so that a position of one of second control points in a second cross section of a model of the object for the second time is identical to a position of a corresponding first control point in a cross section after the expansion or reduction for the second time, and another first control point in the image of the cross section of the object for the second time, which corresponds to the other second control point, is on a straight line passing through the two second control points in the second cross section for the second time; and (E) superimposing the image of the cross section of the object after the second transformation processing for the second time and the second cross section of the object.

Thus, the image of the cross section of the object may be handled as a main processing target.

Incidentally, it is possible to create a program causing a computer to execute the aforementioned processing, and such a program is stored in a computer readable storage medium or storage device such as a flexible disk, CD-ROM, DVD-ROM, magneto-optic disk, a semiconductor memory, and hard disk. In addition, the intermediate processing result is temporarily stored in a storage device such as a main memory or the like.

All examples and conditional language recited herein are intended for pedagogical purposes to aid the reader in understanding the invention and the concepts contributed by the inventor to furthering the art, and are to be construed as being without limitation to such specifically recited examples and conditions, nor does the organization of such examples in the specification relate to a showing of the superiority and inferiority of the invention. Although the embodiments of the present inventions have been described in detail, it should be understood that the various changes, substitutions, and alterations could be made hereto without departing from the spirit and scope of the invention.

What is claimed is:

1. A non-transitory computer-readable storage medium storing a program for causing a processor of a display processing apparatus coupled to a measurement apparatus for measuring cross-sections of a cardiac muscle of a heart to execute a process, the process comprising:

accepting designation of two first control points in a first cardiac muscle model cross-section that is a cross-section of a generated cardiac muscle model of the heart at a reference time, wherein each of the two first control points corresponds to a position of either of two second control points in a first input measured image that is a cross-section image of the heart measured at the reference time;

performing a first transformation processing for the first cardiac muscle model cross-section so that the position of the second control point in the first input measured image is identical to the position of a corresponding first control point in the first cardiac muscle cross-section model;

performing a plurality of second transformation processings at a plurality of next second times that each includes a same calculation as the first transformation processing for a plurality of corresponding second cardiac muscle model cross-sections at each next second time that is a time after the reference time, wherein each second cardiac muscle model cross-section at each next second time is a cross-section of the generated cardiac muscle model of the heart at each next second time and has two third control points with positions that correspond to the positions of the two first control points, and each of the two third control points corresponds to either of two fourth control points in corresponding second input measured images at each next second time;

after completion of the performing the plurality of second transformation processings for the second cardiac muscle model cross-sections, first generating a display of a first superimposed image generated by superimposing the first input measured image at the reference time and the first cardiac muscle model cross-section after the first transformation processing;

performing at least one third transformation processing different from the first and second transformation processings, for at least one of the corresponding second cardiac muscle model cross-sections at a next second time among the plurality of next second times, so that a position of one of two fourth control points in the corresponding second input measured image at the next second time is identical to and fixed on a position of a corresponding third control point in the at least one corresponding second cardiac muscle model cross-section after the second transformation processing, and another third control point in the at least one corresponding second cardiac muscle model cross-section after the second transformation processing is located on a straight line that passes through the two fourth control points in the corresponding second input measured image at the next second time; and second generating a corresponding display of a second superimposed image by superimposing the corresponding second input measured image at the next second time and the at least one corresponding second cardiac muscle model cross-section, after the at least one third transformation processing, wherein the at least one third transformation processing is repeatable for other next second time among the plurality of next second times to repeat a second generating a corresponding display of a second superimposed image for the other next second time.

2. The non-transitory computer-readable storage medium as set forth in claim 1, wherein the process further comprises:

extracting input measured images or cardiac muscle model cross-sections according to an input frame interval of the input images or a time interval of the cardiac muscle models of the hearts.

3. An image processing method executed by a processor of a display processing apparatus coupled to a measurement apparatus for measuring cross-sections of a cardiac muscle of a heart, the method comprising:

accepting, by using the processor, designation of two first control points in a first cardiac muscle model cross-section that is a cross-section of a generated cardiac muscle model of the heart at a reference time, wherein each of the two first control points corresponds to a position of either of two second control points in a first input measured image that is a cross-section image of the heart measured at the reference time;

performing, by using the processor, a first transformation processing for the first cardiac muscle model cross-section so that the position of the second control point in the first input measured image is identical to the position of a corresponding first control point in the first cardiac muscle cross-section model;

performing, by using the processor, a plurality of second transformation processings at a plurality of next second times that each includes a same calculation as the first transformation processing for a plurality of corresponding second cardiac muscle model cross-sections at each next second time that is a time after the reference time, wherein each second cardiac muscle model cross-section at each next second time is a cross-section of the generated cardiac muscle model of the heart at each next second time and has two third control points with positions that correspond to the positions of the two first control points, and each of the two third control points corresponds to either of two fourth control points in corresponding second input measured images at each next second time;

after completion of the performing the plurality of second transformation processings for the second cardiac muscle model cross-sections, first generating, by using the processor, a display of first superimposed image generated by superimposing the first input measured image at the reference time and the first cardiac muscle model cross-section after the first transformation processing;

performing, by using the processor, at least one third transformation processing different from the first and second transformation processings, for at least one of the corresponding second cardiac muscle model cross-section at a next second time among the plurality of next second times, so that a position of one of two fourth control points in the corresponding second input measured image at the next second time is identical to and fixed on a position of a corresponding third control point in the at least one corresponding second cardiac muscle model cross-section after the second transformation processing, and another third control point in the at least one corresponding second cardiac muscle model cross-section after the second transformation processing is located on a straight line that passes through the two fourth control points in the corresponding second input measured image at the next second time; and second generating, by using the processor, a corresponding display of a second superimposed image by superimposing the corresponding second input measured image at the next second time and the at least one corresponding second cardiac muscle model cross-section, after the at least one third transformation processing, wherein the at least one third transformation processing is repeatable for other next second time among the plurality of next second times to repeat a second generating a corresponding display of a second superimposed image for the other next second time.

4. An image processing apparatus coupled to a measurement apparatus for measuring cross-sections of a cardiac muscle of a heart, comprising:

a memory; and a processor configured to use the memory and execute a process, the process comprising:

accepting designation of two first control points in a first cardiac muscle model cross-section that is a cross-section of a generated cardiac muscle model of the heart at a reference time, wherein each of the two first control points corresponds to a position of either of two second control points in a first input measured image that is a cross-section image of the heart measured at the reference time;

performing a first transformation processing for the first cardiac muscle model cross-section so that the position of the second control point in the first input measured image is identical to the position of a corresponding first control point in the first cardiac muscle cross-section model;

performing a plurality of second transformation processings at a plurality of next second times that each includes a same calculation as the first transformation processing for a plurality of corresponding second cardiac muscle model cross-sections at each next second time that is a time after the reference time, wherein each second cardiac muscle model cross-section at each next second time is a cross section of the generated cardiac muscle model of the heart at each next second time and has two third control points with positions that correspond to the positions of the two first control points, and each of the two third control points corresponds to either of two fourth control points in corresponding second input measured images at each next second time;

after completion of the performing the plurality of second transformation processings for the second cardiac muscle model cross-sections, first generating a display of a first superimposed image generated by superimposing the first input measured image at the reference time and the first cardiac muscle model cross-section after the first transformation processing;

performing at least one third transformation processing different from the first and second transformation processings, for at least one of the corresponding second cardiac muscle model cross-sections at a next second time among the plurality of next second times, so that a position of one of two fourth control points in the corresponding second input measured image at the next second time is identical to and fixed on a position of a corresponding third control point in the at least one corresponding second cardiac muscle model cross-section after the second transformation processing, and another third control point in the at least one corresponding second cardiac muscle model cross-section after the second transformation processing is located on a straight line that passes through the two fourth control points in the corresponding second input measured image at the next second time; and second generating a corresponding display of a second superimposed image by superimposing the corresponding second input measured image at the next second time and the at least one corresponding second cardiac muscle model cross-section, after the at least one third transformation processing, wherein the at least one third transformation processing is repeatable for other next second time among the plurality of next second times to repeat a second generating a corresponding display of a second superimposed image for the other next second time.

* * * * *